United States Patent [19]
Di Girolamo et al.

[11] Patent Number: 6,011,191
[45] Date of Patent: Jan. 4, 2000

[54] PROCESS FOR THE PRODUCTION OF HYDROCARBONS WITH A HIGH OCTANE NUMBER BY THE SELECTIVE DIMERIZATION OF ISOBUTENE

[75] Inventors: Marco Di Girolamo, San Donato Milanese; Lorenzo Tagliabue, Cusano Milanino, both of Italy

[73] Assignee: Snamprogetti S.p.A., San Donato Milanese, Italy

[21] Appl. No.: 09/079,292

[22] Filed: May 15, 1998

[30] Foreign Application Priority Data

May 15, 1997 [IT] Italy .................................. MI97A1129

[51] Int. Cl.[7] .............................. C07C 2/24; C07C 2/02; C07C 2/04
[52] U.S. Cl. ........................... 585/514; 585/510; 585/515; 585/520; 585/525; 585/526; 585/529
[58] Field of Search ..................................... 585/510, 514, 585/515, 520, 525, 526, 529

[56] References Cited

U.S. PATENT DOCUMENTS 4,100,220  7/1978  Bowman et al. ............... 260/683.15 R
4,447,668  5/1984  Smith, Jr. et al. ..................... 585/639

FOREIGN PATENT DOCUMENTS 0 467 345   1/1992   European Pat. Off. .
0 745 576  12/1996   European Pat. Off. .

Primary Examiner—Walter D. Griffin
Assistant Examiner—In Suk Bullock
Attorney, Agent, or Firm—Oblon, Spivak, McClelland, Maier & Neustadt, P.C.

[57] ABSTRACT

A process is described for the production of hydrocarbons with a high octane number starting from hydrocarbon cuts containing isobutene by selective dimerization with acid catalysts characterized in that the dimerization reaction is carried out in the presence of primary alcohols and alkyl others in such a quantity as to have in the feeding a molar ratio primary alcohols+alkyl ethers/isobutene of more than 0.1 and a molar ratio primary alcohols/isobutene of less than 0.2, operating, preferably, at a reaction temperature of between 30 and 120° C., at a pressure of less than 5 MPa and feeding space velocities of less than 30 $h^{-1}$.

14 Claims, 1 Drawing Sheet

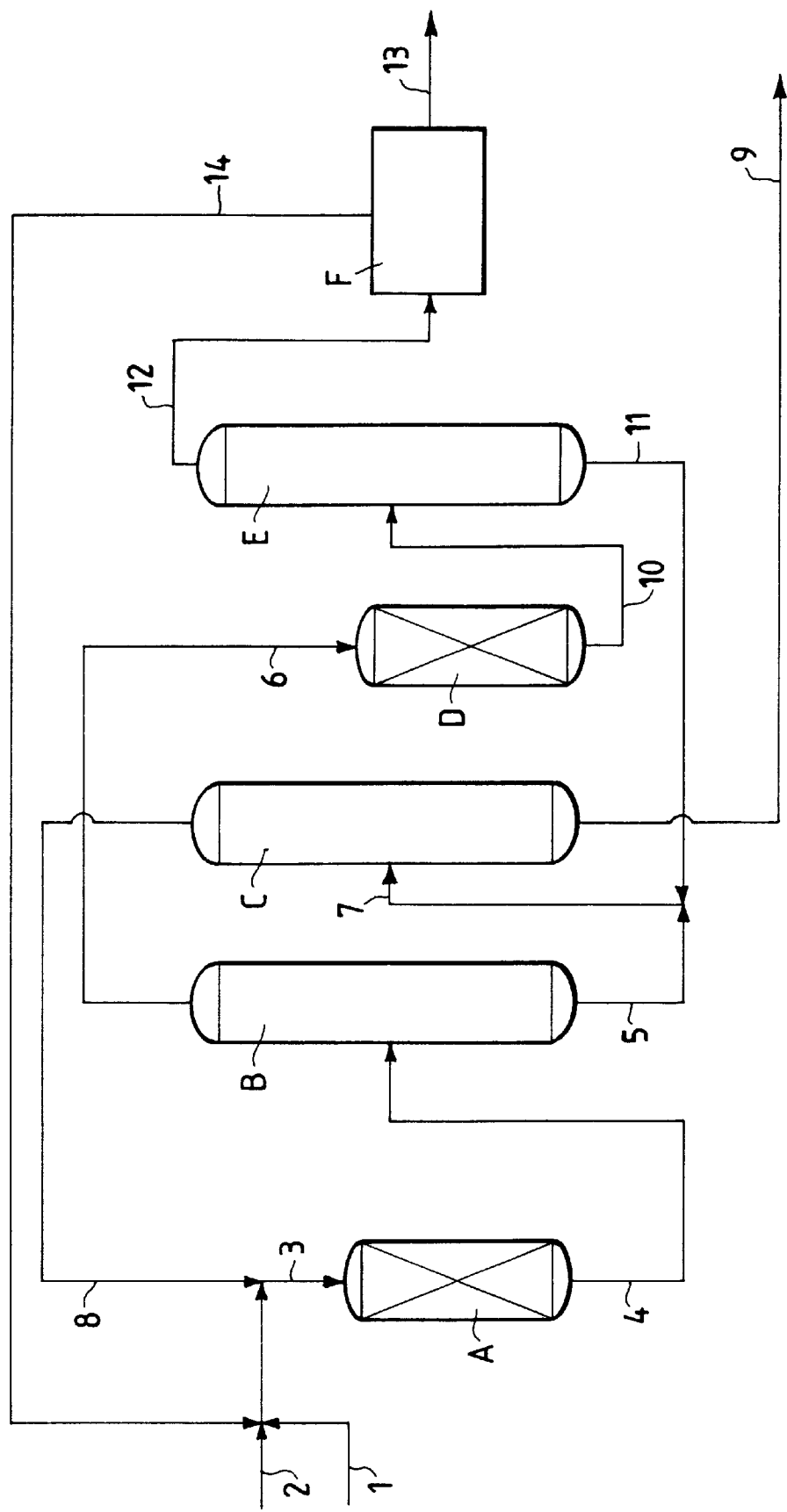

PROCESS FOR THE PRODUCTION OF HYDROCARBONS WITH A HIGH OCTANE NUMBER BY THE SELECTIVE DIMERIZATION OF ISOBUTENE

The present invention relates to a process for the production of hydrocarbons with a high octane number, obtained by the selective dimerization reaction of isobutene contained in hydrocarbon cute and to a lesser extent of possible linear butanes, in the presence of moderate quantities of primary alcohols and alkyl ethers, which favour the production of higher selectivities on the part of the catalyst. The mixture obtained can then be hydrogenated with the conventional methods to obtain a product with a further improvement in the octane characteristics.

For reasons of an environmental nature the composition of fuels is being reformulated; the "Clean Air Act Amendments" (CAAA) in the Unites States are providing general regulations which will probably also be adopted with a few variations by other countries in the near future.

In short the general tendency is towards the production of fuels which burn better and have fewer evaporative emissions. The main measures for reaching this objective are the following (for more specific details see for example: G. H. Unzelman, Fuel Reformulation, 31(2), (1993), 41 and D. Sanfilippo, F. Ancillotti, M. Marchionna, Chim. & Ind., 76, (1994), 32 and references contained therein):

oxygenated compounds will have an ever increasing role as fuel components;

the content of aromatic compounds will be greatly reduced, especially in benzene;

there will be a reduction in the volatility of fuels to minimize evaporative losses;

the content of light olefins, photochemically reactive and precursors responsible for the formation of atmospheric ozone, will be reduced;

both the sulfur content and final boiling point of fuels will also be reduced.

All these measures therefore load to the necessity of planning new processes which can positively contribute to fulfilling the above demands.

As well as oxygenated compounds to which the CAAA have assigned a fundamental role in future reformulated fuels both for raising the octane number and supplying oxygen, purely hydrocarbon products are also proving to be particularly attractive.

Among these the alkylate is particularly distinctive as it has a high octane number, a low volatility and is practically without olefins and aromatics. The alkylation process in liquid phase is a reaction between isoparaffinic hydrocarbons, such as for example, isobutane, and olefins, for example propylene, butenes, pentenes and relative mixtures, in the presence of an acid catalyst for the production of $C_7$–$C_9$ hydrocarbons with a high octane number to be used in fuels (see for example: A. Corma, A. Martinez, Catal. Rev.- Sci. Eng., 35, (1993), 483 and references contained therein).

The main problem of the alkylation process is due to the fact that with the increase in environmental regulations both traditional processes (with hydrofluoric acid and sulfuric acid) are having considerable difficulties which makes their future uncertain; the process with hydrofluoric acid owing to the toxicity of this acid, especially in populated areas, and that with sulfuric acid owing to the large production of acid mud and also to the highly corrosive power of the catalyst.

Alternative processes with solid acid catalysts are in the process of being developed but their commercial applicability is still to be proved.

On the other hand a hydrocarbon product of this type is in ever-increasing demand owing to its octane characteristics (high Research Octane Number (RON) and Motor Octane Number (MON) and those relating to its boiling point (poor volatility but low final point) which place it in the category of compositions which are extremely interesting for obtaining fuels that are more compatible with present-day environmental demands.

In addition, hydrocarbon products with a high octane number such as those generated by the alkylation reaction also have a low sensitivity (difference between RON and MON) and it is known that ethers such as MTBE, ETBE, TAME, etc. favourably react to the reduced sensitivity of the fuel, increasing their already high octane number even more.

This means that there are many advantages in combining a saturated hydrocarbon product with a high octane number (such as alkylate) with ethers such as MTBE. In addition the joint presence of considerable quantities of the two products also allows the content of undesired components such as aromatics, olefins and sulfur to be considerably decreased, by dilution.

In refining, an alternative process for obtaining products with similar characteristics to alkylate can be offered by the hydrogenation of the so-called "polymer" fuel.

The oligomerization process (often erroneously called, in the field of refining, polymerization) was widely used in the years 1930–1940 to convert low-boiling $C_3$–$C_4$ olefins into fuels. The process leads to the production of a fuel with a high octane number (RON about 97) but with a high Sensitivity owing to the purely olefinic nature of the product (for more specific details on the process see: J. H. Gary, G. E. Handwerk, "Petroloum Refining: Technology and Economics", 3rd Ed., M. Dekker, New York, (1994), 250).

Typical olefins which are oligomerized are mainly propylene, which gives slightly higher dimers or oligomers depending on the process used, and isobutene which mainly gives dimers but always accompanied by large quantities of higher oligomers.

With particular respect to the oligomerization of isobutene it is known that this reaction can be carried out in batch, in semicontinuous or in continuous, in both gas-solid phase and liquid phase, generally at temperatures of between 50 and 300° C. and at atmospheric pressure or at such pressures as to maintain the reagents in liquid phase, if deemed suitable.

Typical catalysts for the industrial oligomerization of isobutene are represented by phosphoric acid, generally supported on a solid (for example kieselguhr), or acid resins with cation exchange. The latter allow blander conditions of both temperature and pressure to be used than with supported phosphoric acid (100° C. and 1–2 Mpa vs 200–220° C. and 3–10 MPa).

Other catalysts have also been claimed in literature, both liquid acids such as $H_2SO_4$ or sulfonic acid derivatives, and solids such as for example silicoaluminas, mixed oxides, teolites, fluorinated or chlorinated aluminae, etc.; on the other hand none of those catalysts has as yet enabled the setting up of an industrial process as in the case of supported phosphoric acid (F. Asinger, "Mono-olefins: Chemistry and Technology", Pergamon Press, Oxford, pages 435–456) and in that of cationic resins (G. Scharfe, Hydrocarbon Proc., April 1973, 171).

From the product point of view, the main problem of this process lies in the fact that in the oligomerization phase heavy oligomers such as trimers (selectivity of 15–30%) and tetramers (selectivity of 1–2%) of isobutene are produced in excessive percentages. Tetramers are completely outside the fuel fraction as they are too high-boiling and therefore represent a distinct loss in fuel yield; with respect to trimers (or their hydrogenated derivatives) it is desirable to strongly reduce their concentration as their boiling point (170–180° C.) is on the limit of future specifications on the final point of reformulated fuels On the other hand the problem of minimizing the formation of higher oligomers to dimers with percentages of less than 10% is a problem which is typical of the oligomerization of isobutene, as is also specified in literature (C. T. O'Connor, M. Kojima, K. W. Schumann, Appl. Catal., 16 (1985), 193).

This level of heavy compounds is analogous to that of an alkylate and is still tolerated in the fuel pool.

From what has been said above, it is evident that there is a wide interest in obtaining a now dimerization process of isobutene which allows the synthesis of a higher quality product, by reaching greater selectivities.

It has now been surprisingly found that by carrying out the selective dimerization reaction of isobutene in the presence of moderate quantities of primary alcohols and alkyl ethers, the production of a fraction of oligomers is selectively obtained, particularly rich in dimers (>90%) and practically without tetramers and higher oligomers (<0.05%), containing small quantities of dimer ethers.

The reaction product is then preferably hydrogenated to give a completely saturated end-product with a high octane number and low sensitivity. The hydrogenation can be carried out with the conventional methods as described for example in F.Asinger, "Mono-olefins: Chemistry and Technology", Pergamon Press, Oxford, page 455.

As an example, table I indicates the octane numbers and relative boiling points of some of the products obtained with the process of the present invention.

TABLE I

| Product | RON | MON | b. p. (° C.) |
| --- | --- | --- | --- |
| di-isobutenes | 100 | 89 | 100–105 |
| iso-octane | 100 | 100 | 99 |
| tri-isobutenes | 100 | 89 | 175–185 |
| hydrogenated tri-isobutenes | 101 | 102 | 170–180 |

The process of the present invention for the production of hydrocarbons with a high octane number starting from hydrocarbon cuts containing isobutene, by selective dimerization with acid catalysts is characterized in that the reaction in carried out in the presence of primary alcohols in such a quantity as to have in the feeding a molar ratio primary alcohols+alkyl ethers/isobutene of more than 0.1, preferably between 0.1 and 0.7, and a ratio primary alcohol/isobutene of less than 0.2, preferably between 0.005 and 0.1.

It should also be pointed out that in the case of $C_4$ hydrocarbon streams also comprising linear olefins it has been observed that at least a part of the latter can be converted by reaction with isobutene into a hydrocarbon product without threaten their octane number. It is also preferable to carry out an enriching treatment, by means of pre-isomerization, of the internal linear olefins, which would benefit the total octane number of the mixture.

The process claimed herein can be applied to cuts containing isobutane, isobutene, n-butane and n-butenes.

Although a wide variety of sources is available for supplying these streams, the most common ones concern those deriving from dehydrogenation processes of iso-paraffins, from FCC units and streams coming from steam cracking.

When the streams from steam-cracking contain diolefins in addition to the desired mono-olefins, it is necessary to eliminate them by the typical removal treatment (for example extractions or selective hydrogenations).

As well as the hydrocarbon components, the stream comprises as specified above, primary alcohol (in great molar defect with respect to the iso-olefin) and alkyl ether.

The primary alcohol used can be selected from primary alcohols containing from 1 to 6 carbon atoms: methanol and/or ethanol are preferred.

The alkyl ether used can be selected from those containing from 5 to 10 carbon atoms: MTBE (methyl-ter-butyl ether), ETBE (ethyl-ter-butyl ether), MSBE (methyl-sec-butyl ether), ESBE (ethyl-sec-butyl ether) or mixtures of these are preferred.

The isobutene together with the hydrocarbon stream in which it is contained is sent with the primary alcohol and alkyl ether, in strong stoichiometric defect, into contact with the acid catalyst where the dimerization takes place. The primary alcohol is almost completely converted under the reaction conditions to dimer ether.

The presence of a constant level of primary alcohol in the reactors is fundamental for obtaining the desired high selectivities as it enables the use of a catalytic species with the correct activity.

The fact of operating with the correct catalytic activity makes the reaction much more controllable also from a thermal point of view with a consequent improvement in the quality of the product.

The quantity of alkyl ether sent to the reactors is such that, depending on the operating conditions, it can be either further produced or partially decomposed: in the latter case, as the decomposition process is of endothermal ether, a part of the heat developed in the dimerization reaction can be absorbed, thus further improving the temperature control in the reactor. In addition, the alcohol liberated by the decomposition of the ether, as well as interacting with the catalyst, can react with the dimers and butenes present in the reactor.

The optimum level of the sum of primary alcohol and alkyl ether which must be present in the reaction environment to obtain selectivities to dimers close to or higher than 90% by weight, depends on the composition of the hydrocarbon charge.

When the charge consists of $C_4$ hydrocarbon cuts containing isobutene in a quantity of between 10 and 30% by weight and n-butenes in a quantity of between 25 and 50% by weight, it is advisable, to obtain better results, to operate with a molar ratio primary alcohol+alkyl ether/isobutene of between 0.2 and 0.6.

When the charge consists of $C_4$ hydrocarbon cuts containing isobutene in a quantity of between 30 and 60% by weight, n-butenes in a quantity of more than 30% by weight and $C_4$ paraffins in a quantity of less than 15% by weight, it is advisable, to obtain better results, to operate with a molar ratio primary alcohol+alkyl ether/isobutene of between 0.1 and 0.6.

When the charge consists of $C_4$ hydrocarbon cuts containing isobutene in a quantity of between 28 and 60% by weight, $C_4$ paraffins in a quantity of more than 30% by weight and n-butenes in a quantity of less than 10% by weight, it is advisable, to obtain better results, to operate with a molar ratio primary alcohol+alkyl ether/isobutene of between 0.3 and 0.6.

When the charge consists of $C_4$ hydrocarbon cuts containing isobutene in a percentage of more than 80% by weight, it is advisable to obtain better results, to operate with a molar ratio primary alcohol+alkyl ether/isobutene of between 0.5 and 0.7.

Table II indicates the average compositions of typical $C_4$ hydrocarbon fractions coming from different sources (FCC, Steam Cracking, dehydrogenation of isobutane, streams of isobutene with a high concentration).

TABLE II

Typical percentage compositions of $C_4$ streams

| | Steam cracking | FCC | Dehydrogen. | Conc. isobutene |
|---|---|---|---|---|
| Isobutene | 30–46 | 10–25 | 45–55 | >90 |
| n-butenes | 35–60 | 25–50 | | <10 |
| $C_4$ satur. | 4–8 | 30–60 | 45–55 | <10 |

For charges different from those generally available in industrial practice, it can be observed that the addition of considerable quantities of linear olefins with respect to the charge compositions cited above, causes a slight increase in the selectivity to dimers and therefore a limited reduction in the lower limit of the molar ratio primary alcohol+alkyl ether/isobutene previously indicated. On the contrary, an increase in the content of saturated hydrocarbons causes a slight deterioration in the selectivity and therefore the value of the lower limit of the ratio is slightly increased.

A wide variety of acid catalysts can be used for this process, among these, for example, mineral acids such as sulfuric acid, $BF_3$, supported phosphoric acid, suitably modified zeolites, heteropolyacids and sulfonated polymeric resins, for example Amberlyst 15 and Amberlyst 35, etc, can be mentioned. Among these catalysts the use of macrolattice sulfonated resins, generally copolymers of styrene and benzene, is preferred the characteristics of these resins are amply described in literature (see for example A. Mitschker, R.Wagner, P. M. Lange, "Heterogeneous Catalysis and Fine Chemicals", M. Cuisnet ed., Elsevier, Amsterdam (1988), 61).

A wide range of operating conditions can be used for producing hydrocarbons with a high octane number in the desired selectivities by the process of the present invention. It is possible to operate in vapor phase or in liquid-vapor phase but the operation conditions in liquid phase are preferred.

The process of the present invention can operate under both batch and continuous conditions, considering however that the latter are much more advantageous in industrial practice. The reactor configuration selected can be optionally selected from fixed bed, tubular fixed bed, adiabatic, stirred and finally column reactor which also allows the separation of the products (a description on the general use of this technology is provided for example in: J. L. De Carmo, V. N. Paruledar, V. Pinjala, Chem. Eng. Progr., March 1992, 43).

The range of process conditions, operating in liquid phase, comprises a wide variety of operating conditions which are described hereunder.

The pressure in preferably superatmospheric to maintain the reagents in liquid phase, generally below 5 MPa, more preferably between 0.2–2.5 MPa. The reaction temperature is preferably between 30 and 120° C. The feeding space velocities of the alcohol-hydrocarbon stream should preferably be less than 30 $h^{-1}$, more preferably between 1 and 15 $h^{-1}$.

The isobutene is mainly converted in the reaction zone, however also part of the n-olefins can be converted to useful product; for the most part, there are no limits in the concentration of iso-olefin in the hydrocarbon fraction even if it is preferable to have concentrations of between 2 and 60%, there are no limits in the ratio between isobutene and linear olefins. It should be observed that in the case of streams coming from the dehydrogenation of isobutane there are no significant concentrations of linear butenes in the charge.

The process of the present invention can be carried out in particular by means of the following basic steps:

a) feeding to a dimerization reactor the hydrocarbon cut containing isobutene together with a stream consisting of primary alcohols and a stream containing alkyl ethers;

b) sending the product leaving the dimerization reactor to a fractionation column from whose head a stream is obtained containing non-reacted isobutene and small quantities of ethers and alcohols and from the bottom of which a stream containing dimers and alkyl ethers is removed;

c) sending the stream containing non-reacted isobutene to a second reactor to complete the conversion of isobutene;

d) sending the product leaving the second reactor to a second fractionation column from whose head a stream is obtained containing $C_4$ hydrocarbons and primary alcohols and from whose bottom a stream containing $C_4$ hydrocarbons, dimers and alkyl ethers is removed;

e) sending to a third fractionation column the bottom streams removed from the two fractionation columns obtaining the desired hydrocarbon product at the bottom and a stream containing alkyl ethers at the head, which is recycled to the first reactor;

f) sending the stream leaving the head of the second fractionation column to a separation unit of the primary alcohols which are subsequently recycled to the first reactor.

A recommended process scheme is shown in the enclosed figure to provide a clearer illustration of the present invention.

The stream (1) containing isobutene, joined to the feeding of primary alcohol (2) (methanol), is sent to a first reactor (A) in which the $C_4$ iso-olefin is selectively converted to dimers.

The effluent (4) from the reactor (A) is sent to a separation column (B) where a stream (6) is removed at the head, essentially containing non-converted olefins, alkyl ether (MTBE) and alcohol (methanol) in such quantities an to satisfy the molar ratios specified above, whereas at the bottom a stream (5) is removed essentially containing dimers, oligomers, ethers of dimers and alkyl ether (MTBE).

This stream (5) is sent to a separation column (C) where a stream is removed at the head, essentially containing alkyl ether (MTBE) recycled to the reactor (A), whereas at the bottom the synthesis product is obtained essentially consisting of dimers and small quantities of oligomers and ethers of dimers.

The stream (6) is fed to a second reactor (D) in which the isobutene present is selectively converted to dimers. The effluent (10) from the reactor (D) is separated in a column (E) from which a bottom stream (11) is removed, essentially containing alkyl ether (MTSE) and dimers, which is sent, together with the stream (5), to the column (C).

Optionally, the stream (12) at the head can be treated to remove the alcohol (methanol) contained therein in a unit (F) which can consist for example of an absorption system of the primary alcohol on molecular sieves or an extraction of the alcohol itself with water. In both cases the alcohol recovered can be sent (14) to the reaction, whereas the hydrocarbon stream (13) can be used in subsequent operations.

An example is now provided for a better illustration of the invention without limiting its scope in any way.

EXAMPLE 1

With reference to the diagram in the FIGURE, a hydrocarbon stream containing 50% by weight of isobutene, of the type obtained by the dehydrogenation of isobutane, is converted in the presence of suitable quantities of methanol and MTBE into a hydrocarbon product with a high octane number containing about 90% by weight of di-isobutenes, the rest consisting of trimers of isobutenes and ethers of di-isobutenes.

Tables XII and IV show with reference to the enclosed FIGURE, the quantities of the various streams of the plant indicated in kg/h, % weight, Kmol/h and % mol.

The reactors (A) and (D) operate at a temperature at the outlet of 70° C. and 75° C. respectively and both at an operating pressure of 2 MPa.

The molar ratio methanol+MTBE/isobutene is 0.375 in reactor (A) and 0.154 in reactor (B).

The corresponding molar ratios methanol/isobutene are 0.008 in reactor (A) and 0.017 in reactor (B).

The catalyst used is a commercial macroporous sulfonated resin of the typo Amerlyst 35 produced by Rohm & Haas, Co.

TABLE III

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Kg/h |
| Isobutene | 1000.0 | 0.0 | 1008.5 | 98.2 | 0.0 | 96.2 | 8.5 | 8.5 | 0.0 | 12.5 | 8.5 | 4.0 | 4.0 | 0.0 |
| Isobutane | 1000.0 | 0.0 | 1070.4 | 1070.4 | 0.0 | 1070.4 | 70.4 | 70.4 | 0.0 | 1070.4 | 70.4 | 1000.0 | 1000.0 | 0.0 |
| C8 | 0.0 | 0.0 | 12.9 | 629.8 | 629.8 | 0.0 | 909.3 | 12.9 | 896.4 | 79.5 | 79.5 | 0.0 | 0.0 | 0.0 |
| C12 | 0.0 | 0.0 | 0.0 | 83.5 | 83.5 | 0.0 | 91.6 | 0.0 | 91.6 | 8.1 | 8.1 | 0.0 | 0.0 | 0.0 |
| Methanol | 0.0 | 2.3 | 4.6 | 1.0 | 0.0 | 1.0 | 0.0 | 0.0 | 0.0 | 2.3 | 0.0 | 2.3 | 0.0 | 2.3 |
| MTBE | 0.0 | 0.0 | 561.9 | 586.1 | 564.9 | 21.2 | 581.9 | 581.9 | 0.0 | 16.9 | 16.9 | 0.0 | 0.0 | |
| C9 Ethers | 0.0 | 0.0 | 0.0 | 9.3 | 9.3 | 0.0 | 10.2 | 0.0 | 10.2 | 0.9 | 0.9 | 0.0 | 0.0 | 0.0 |
|  | 2000.0 | 2.3 | 2678.3 | 2676.3 | 1487.6 | 1190.7 | 1672.0 | 673.7 | 998.3 | 1190.7 | 184.4 | 1006.3 | 1004.0 | 2.3 |
| % weight |
| Isobutene | 50.00 | 0.00 | 37.65 | 3.67 | 0.00 | 8.24 | 0.51 | 1.26 | 0.00 | 1.05 | 4.61 | 0.40 | 0.40 | 0.00 |
| Isobutane | 50.00 | 0.00 | 39.97 | 39.91 | 0.00 | 89.90 | 4.21 | 10.46 | 0.00 | 69.90 | 36.19 | 99.38 | 99.60 | 0.00 |
| C8 | 0.00 | 0.00 | 0.48 | 30.98 | 55.78 | 0.00 | 54.39 | 1.92 | 89.79 | 6.68 | 43.11 | 0.00 | 0.00 | 0.00 |
| C12 | 0.00 | 0.00 | 0.00 | 3.12 | 5.61 | 0.00 | 5.48 | 0.00 | 9.18 | 0.66 | 4.41 | 0.00 | 0.00 | 0.00 |
| Methanol | 0.00 | 100.00 | 0.17 | 0.04 | 0.00 | 0.06 | 0.00 | 0.00 | 0.00 | 0.19 | 0.01 | 0.23 | 0.00 | 100.00 |
| MTBE | 0.00 | 0.00 | 21.72 | 21.88 | 37.98 | 1.76 | 34.80 | 86.36 | 0.00 | 1.42 | 9.18 | 0.00 | 0.00 | 0.00 |
| C9 Ethers | 0.00 | 0.00 | 0.00 | 0.35 | 0.63 | 0.00 | 0.61 | 0.00 | 1.03 | 0.08 | 0.49 | 0.00 | 0.00 | 0.00 |
|  | 100.00 | 100.00 | 100.00 | 100.00 | 100.00 | 100.00 | 100.00 | 100.00 | 100.00 | 100.00 | 100.00 | 100.00 | 100.00 | 100.00 |

TABLE IV

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Kmol/h |
| Isobutene | 17.825 | 0.000 | 17.997 | 1.750 | 0.000 | 1.750 | 0.152 | 0.151 | 0.000 | 0.223 | 0.152 | 0.071 | 0.071 | 0.000 |
| Isobutane | 17.206 | 0.000 | 18.418 | 0.000 | 0.000 | 18.418 | 1.212 | 1.212 | 0.000 | 18.418 | 1.212 | 17.206 | 17.206 | 0.000 |
| C8 | 0.000 | 0.000 | 0.115 | 7.396 | 7.396 | 0.000 | 8.105 | 0.115 | 7.989 | 0.709 | 0.709 | 0.000 | 0.000 | 0.000 |
| C12 | 0.000 | 0.000 | 0.000 | 0.496 | 0.496 | 0.000 | 0.544 | 0.000 | 0.544 | 0.048 | 0.048 | 0.000 | 0.000 | 0.000 |
| Methanol | 0.000 | 0.071 | 0.143 | 0.030 | 0.000 | 0.030 | 0.000 | 0.000 | 0.000 | 0.072 | 0.000 | 0.071 | 0.000 | 0.071 |
| MTBE | 0.000 | 0.000 | 6.601 | 6.649 | 6.409 | 0.240 | 6.601 | 6.601 | 0.000 | 0.192 | 0.192 | 0.000 | 0.000 | 0.000 |
| C9 Ethers | 0.000 | 0.000 | 0.000 | 0.065 | 0.065 | 0.000 | 0.071 | 0.000 | 0.071 | 0.006 | 0.006 | 0.000 | 0.000 | 0.000 |
|  | 35.03 | 0.07 | 43.25 | 34.80 | 14.37 | 20.44 | 16.68 | 8.08 | 8.61 | 19.67 | 2.32 | 17.35 | 17.28 | 0.07 |
| % mol |
| Isobutene | 50.68 | 0.00 | 41.56 | 5.03 | 0.00 | 8.56 | 0.91 | 1.87 | 0.00 | 1.13 | 6.53 | 0.41 | 0.41 | 0.00 |
| Isobutane | 49.12 | 0.00 | 42.58 | 52.92 | 0.00 | 90.12 | 7.26 | 15.00 | 0.00 | 93.64 | 52.26 | 99.18 | 99.59 | 0.00 |
| C8 | 0.00 | 0.00 | 0.27 | 21.25 | 51.48 | 0.00 | 48.57 | 1.43 | 92.84 | 43.60 | 30.55 | 0.00 | 0.00 | 0.00 |
| C12 | 0.00 | 0.00 | 0.00 | 1.43 | 3.45 | 0.00 | 3.26 | 0.00 | 6.33 | 0.25 | 2.08 | 0.00 | 0.00 | 0.00 |
| Methanol | 0.00 | 100.00 | 0.33 | 0.09 | 0.00 | 0.15 | 0.00 | 0.00 | 0.00 | 0.37 | 0.02 | 0.41 | 0.00 | 100.00 |
| MTBE | 0.00 | 0.00 | 15.26 | 19.10 | 44.61 | 1.17 | 39.56 | 61.70 | 0.00 | 0.96 | 6.26 | 0.00 | 0.00 | 0.00 |
| C9 Ethers | 0.00 | 0.00 | 0.00 | 0.19 | 0.45 | 0.00 | 0.43 | 0.00 | 0.83 | 0.03 | 0.27 | 0.00 | 0.00 | 0.00 |
|  | 100.00 | 100.00 | 100.00 | 100.00 | 100.00 | 100.00 | 100.00 | 100.00 | 100.00 | 100.00 | 100.00 | 100.00 | 100.00 | 100.00 |

We claim:

1. A process for the production of hydrocarbons with a high octane number starting from hydrocarbon cuts containing isobutene, by selective dimerization with acid catalysts characterized in that the dimerization reaction is carried out in the presence of primary alcohols and alkyl ethers in such a quantity as to have in the feeding a molar ratio primary alcohols+alkyl ethers/isobutene of more than 0.1 and a molar ratio primary alcohols/isobutene of less than 0.2.

2. The process according to claim 1, operating, at a reaction temperature of between 30 and 120° C., at a pressure of less than 5 MPa and feeding space velocities of less than 30 $h^{-1}$.

3. The process according to claim 1 wherein the molar ratio in the feeding of primary alcohols+alkyl ethers/isobutene in between 0.1 and 0.7.

4. The process according to claim 1 wherein the molar ratio in the feeding of primary alcohols/isobutene is between 0.05 and 0.1.

5. The process according to claim 1 wherein the charge consists of hydrocarbon cuts containing isobutene in a quantity of between 10 and 30% by weight and n-butenes in a quantity of between 25 and 50% by weight and the molar ratio primary alcohols+alkyl ethers/isobutene is between 0.2 and 0.6.

6. The process according to claim 1 wherein the charge consists of hydrocarbon cuts containing isobutene in a quantity of between 30 and 60% by weight and n-butenes in a quantity of more than 30% by weight and $C_4$ paraffins in a quantity of less than 15% by weight and the molar ratio primary alcohols+alkyl ethers/isobutene is between 0.1 and 0.6.

7. The process according to claim 1 wherein the charge consists of hydrocarbon cuts containing isobutene in a quantity of between 30 and 60% by weight and $C_4$ paraffins in a quantity of more than 30% by weight and n-butenes in a quantity of less than 10% by weight and the molar ratio primary alcohols+alkyl ethers/isobutene is between 0.3 and 0.6.

8. The process according to claim 1 wherein the charge consists of hydrocarbon cuts containing isobutene in quantities of more than 80% by weight and the molar ratio primary alcohols+alkyl ethers/isobutene is between 0.5 and 0.7.

9. The process according to claim 1 wherein the space velocities in the feeding are between 1 and 15 $h^{-1}$.

10. The process according to claim 1 wherein the primary alcohol has from 1 to 6 carbon atoms.

11. The process according to claim 10 wherein the primary alcohol is selected from methanol and/or ethanol.

12. The process according to claim 1 wherein the alkyl ether has from 5 to 10 carbon atoms.

13. The process according to claim 12 wherein the alkyl ether is selected from MTBE, ETBE, MSBE, ESBE or mixtures of these.

14. The process according to any one of claims 1 to 13 comprising the following basic steps:

a) feeding to a dimerization reactor the hydrocarbon cut containing isobutene together with a stream consisting of primary alcohols and a stream containing alkyl ethers;

b) sending the product leaving the dimerization reactor to a fractionation column from whose head a stream is obtained containing non-reacted isobutene and small quantities of ethers and alcohols and from the bottom of which a stream containing dimers and alkyl ethers is removed;

c) sending the stream containing the non-reacted isobutene to a second reactor to complete the conversion of isobutene;

d) sending the product leaving the second reactor to a second fractionation column from whose head a stream is obtained containing $C_4$ hydrocarbons and primary alcohols and from whose bottom a stream containing $C_4$ hydrocarbon, dimers and alkyl ethers is removed;

e) sending to a third fractionation column the bottom streams removed from the two fractionation columns obtaining the desired hydrocarbon product at the bottom and a stream containing alkyl ethers at the head, which is recycled to the first reactor;

f) sending the stream leaving the head of the second fractionation column to a separation unit of the primary alcohols which are subsequently recycled to the first reactor.

* * * * *